(12) United States Patent
Taheri et al.

(10) Patent No.: US 9,568,442 B2
(45) Date of Patent: Feb. 14, 2017

(54) STRAIN MAPPING IN TEM USING PRECESSION ELECTRON DIFFRACTION

(71) Applicants: Mitra Lenore Taheri, Philadelphia, PA (US); Asher Calvin Leff, Philadelphia, PA (US)

(72) Inventors: Mitra Lenore Taheri, Philadelphia, PA (US); Asher Calvin Leff, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/890,560

(22) PCT Filed: May 23, 2014

(86) PCT No.: PCT/US2014/039293
§ 371 (c)(1),
(2) Date: Nov. 11, 2015

(87) PCT Pub. No.: WO2014/190239
PCT Pub. Date: Nov. 27, 2014

(65) Prior Publication Data
US 2016/0139063 A1     May 19, 2016

Related U.S. Application Data

(60) Provisional application No. 61/827,356, filed on May 24, 2013.

(51) Int. Cl.
| G01N 23/20 | (2006.01) |
| G01N 23/02 | (2006.01) |
| G01L 1/25 | (2006.01) |
| G01N 23/04 | (2006.01) |
| H01J 37/26 | (2006.01) |

(52) U.S. Cl.
CPC ......... *G01N 23/20058* (2013.01); *G01L 1/25* (2013.01); *G01N 23/02* (2013.01); *G01N 23/04* (2013.01);
(Continued)

(58) Field of Classification Search
None
See application file for complete search history.

(56) References Cited

U.S. PATENT DOCUMENTS

| 7,084,400 | B2* | 8/2006 | Soeda | ................... | G01N 23/046 250/307 |
| 8,552,372 | B2* | 10/2013 | Nojima | .............. | G01N 23/2055 250/306 |

(Continued)

FOREIGN PATENT DOCUMENTS

WO    WO2010052289 A1    5/2010

OTHER PUBLICATIONS

Kobler et al, "ACOM-TEM and its application for the investigation of deformation pathways in nanocrystalline Pd and AuPd", The 16th European Microscopy Congress, Lyon, France. http://emc-proceedings.com/abstract/acom-tem-and-itsapplication-for-the-investigation-of-deformation-pathways-in-nanocrystalline-pd-and-aupd/.*

(Continued)

*Primary Examiner* — Jack Berman
(74) *Attorney, Agent, or Firm* — Mendelsohn Dunleavy, P.C.

(57) ABSTRACT

A sample material is scanned with a transmission electron microscope (TEM) over multiple steps having a predetermined size at a predetermined angle. Each scan at a predetermined step and angle is compared to a template, wherein the template is generated from parameters of the material and the scanning. The data is then analyzed using local (Continued)

mis-orientation mapping and/or Nye's tensor analysis to provide information about local strain states.

20 Claims, 27 Drawing Sheets

(52) U.S. Cl.
CPC ............... *G01N 23/20* (2013.01); *H01J 37/26* (2013.01); *G01N 2223/03* (2013.01); *G01N 2223/0565* (2013.01); *G01N 2223/0566* (2013.01); *G01N 2223/418* (2013.01); *G01N 2223/607* (2013.01)

(56) References Cited

U.S. PATENT DOCUMENTS

| | | | | |
|---|---|---|---|---|
| 9,274,070 | B2* | 3/2016 | Weiss | H01J 37/26 |
| 2003/0006373 | A1* | 1/2003 | Koguchi | H01J 37/2955 |
| | | | | 250/311 |
| 2010/0108883 | A1 | 5/2010 | Zewail | |
| 2010/0158392 | A1* | 6/2010 | Adams | B82Y 30/00 |
| | | | | 382/218 |
| 2011/0220796 | A1 | 9/2011 | Nicolopoulos et al. | |

OTHER PUBLICATIONS

Kobler et al., "Combination of insitu straining and ACOM-TEM: A novel method for analysis of plastic deformation of nanocrystalline metals", Ultramicroscopy, vol. 128, May 2013, pp. 68-81.*

Leff et al. "Estimation of dislocation density from precession electron diffraction data using the Nye tensor", Ultramicroscopy, vol. 153, Jun. 2015, pp. 9-21.*

International Search Report and Written Opinion; mailed Sep. 24, 2014 for PCT Application No. PCT Application No. PCT/US2014/039293.

Wilkinson, A. J., et al. "High-resolution electron backscatter diffraction: An emerging tool for studying local deformation." The Journal of Strain Analysis for Engineering Design 45.5 (2010): 365-376.

Brewer, L. N., et al. "Misorientation mapping for visualization of plastic deformation via electron back-scattered diffraction." Microscopy and Microanalysis 12.01 (2006): 85-91.

Wilkinson, Angus J. "Assessment of lattice strain, rotation and dislocation content using electron back-scatter diffraction." Journal of Physics: Conference Series. vol. 326. No. 1. IOP Publishing, 2011.

Hernández-Rivera, J. L., et al. "Evaluation of strain caused by coherent precipitates in an Al alloy using TEM techniques." Materials Characterization 73 (2012): 61-67.

Hÿtch, M. J., et al. "Quantitative measurement of displacement and strain fields from HREM micrographs." Ultramicroscopy 74.3 (1998): 131-146.

Johnson, C. L., et al. "Nanoscale waviness of low-angle grain boundaries." Proceedings of the National Academy of Sciences 101.52 (2004): 17936-17939.

Rauch, E. F., et al. "Coupled microstructural observations and local texture measurements with an automated crystallographic orientation mapping tool attached to a TEM." Materialwissenschaft und werkstofftechnik 36.10 (2005): 552-556.

* cited by examiner

STRAIN MAPPING IN TEM USING PRECESSION ELECTRON DIFFRACTION

This application claims the benefit of U.S. Provisional Application No. 61/827,356 filed May 24, 2013, the contents of which are hereby incorporated by reference.

STATEMENT OF GOVERNMENT INTEREST

This invention was made with government support under Contract Nos. DE-SC0008274 and DE-NE0000315 (Nuclear Energy University Program) awarded by the Department of Energy; and Contract No. CMMI-1150807 awarded by the National Science Foundation. The government has certain rights in the invention.

BACKGROUND OF THE INVENTION

1. Field of the Invention

The present invention is directed to the field of material analysis. In particular the field of the invention is directed to strain mapping of materials.

2. Description of the Related Technology

Measurement of strain in crystalline materials is of interest for several reasons. Local strain can have an effect on the properties and performance of materials, but also, it often serves as a driving force for microstructural evolution. Microstructural evolution is the change in the internal structure of the material, as in the positions of the atoms relative to one another, both in terms of their immediate neighbors and on a longer scale. Increased dislocation densities provide greater strength and hardness, but a decrease in ductility. Thermomechanical processes such as rolling and annealing rely on the stored energy from dislocations to act as the driving force for recovery and recrystallization. By controlling these processes, finely tuned microstructures can be produced to meet specific requirements. Quantifying dislocation densities is crucial to understanding deformation, recovery, and recrystallization and the specific mechanisms that drive them.

In analyzing the strain in materials, a number of techniques exist. A primary technique available for strain measurement on the nanoscale is geometric phase analysis (GPA). GPA is a post-imaging process for mapping of strain in a high resolution TEM (transmission electron microscope). GPA can achieve very accurate results at sub-nanometer resolution. GPA also allows for precise measurement of elastic strain that occurs independently or due to the distortion caused by defects introduced through plastic strain, i.e. dislocations. However, a drawback of GPA is that it requires that the high resolution TEM image being used was taken on a zone axis such that the lattice of the material is directly visible, and that there is a strain-free reference area contained within the image.

GPA may be used for mapping the strain around individual defects in an otherwise perfect crystal. For example the strain fields associated with the dislocations that make up a low angle grain boundary. This limits the usefulness of GPA with respect to polycrystalline materials and thicker specimens where such high resolution is not always attainable. Furthermore, it is difficult to capture a region that is truly free of strain to use for a reference, especially in the same frame as the defect that is targeted.

In addition to GPA, there are other small-scale strain mapping techniques available, such as various post analyses of scanning electron microscope (SEM), EBSD maps, holographic interferometry in TEM, or X-ray diffraction strain imaging.

Despite improvements in resolution, SEMs are limited to a minimum spatial resolution of approximately 40 nm. This drawback, along with its nature as a surface characterization technique, makes SEM less than ideal for measuring dislocations.

Dark-field holographic interferometry is an improvement on GPA because it is capable of capturing a larger field of view with a similar resolution as that of GPA. However, it is limited in terms of what samples it is applicable to; specifically, the sample must consist of a cross-section of unstrained substrate and a strained film such as that produced by molecular beam epitaxy. While this sample geometry may be found in microelectronic devices, it is not possible to achieve this geometry for bulk polycrystalline materials.

The primary drawback to strain imaging using X-ray diffraction (XRD) is that while it is possible to measure average strain with accuracy on a typical XRD instrument, in order to achieve a spatial resolution on a nanometer scale a synchrotron source must be used. Additionally, the resolutions achieved are not as high as those capable of being achieved with existing TEM strain mapping techniques.

There are a number of approaches to measuring the strain using EBSD. Strain in the crystal lattice leads to slight changes in the Kikuchi patterns. However these slight changes are difficult to detect, especially at the low resolutions used for rapid pattern acquisition over a large scan area. EBSD techniques are limited by the resolution of backscatter detectors and the relatively large step sizes used in EBSD scans. In recent experiments performed on copper bi-crystals, the best case lateral and longitudinal resolution for an EBSD scan was determined to be 34 by 45 nm.

Another method is described in the publication WO 2010/052289. This reference describes a method and device for electron diffraction tomography of a crystal sample which employs scanning of an electron beam over a plurality of discrete locations of the sample in combination with a beam scanning protocol, as the beam converges at each discrete location of the sample to obtain a series of electron diffraction patterns, use of template matching is performed to determine crystal orientations and thickness maps to in order to obtain a common intensity scaling factor. The disclosure of WO 2010/052289 is hereby incorporated by reference to the extent that it provides details of electron diffraction tomography and template matching.

While the above described methods for strain mapping are useful, there is still a need for improved methods of producing strain maps of materials.

SUMMARY OF THE INVENTION

The present invention provides a method for strain mapping a material.

An aspect of the invention may be a method for strain mapping a material comprising: scanning a sample of a material with a transmission electron microscope (TEM), wherein the scanning of the material occurs over multiple steps having a step size and at a beam precession angle. The method also comprises comparing each scan at a step and beam precession angle to a template to produce data, wherein the template is generated from parameters of the material and the scanning. The method further comprises analyzing the data using local mis-orientation mapping analysis or Nye tensor analysis; and producing a strain map of the sample.

Another aspect of the invention is a method for strain mapping a material comprising: scanning a sample of a material with a microscope, wherein the scanning of the material occurs over multiple steps having a step size at an angle. The method further comprises comparing each scan at a step and angle to a template, wherein the template is generated from parameters of the material and the scanning. The method further comprises analyzing the data using Nye tensor analysis, wherein a best fit of a Nye tensor for each predetermined step is calculated; and producing a local strain map of the sample.

BRIEF DESCRIPTION OF THE DRAWINGS

FIG. 10B is at an increased magnification.

DETAILED DESCRIPTION OF THE PREFERRED EMBODIMENT(S)

Figure 1:
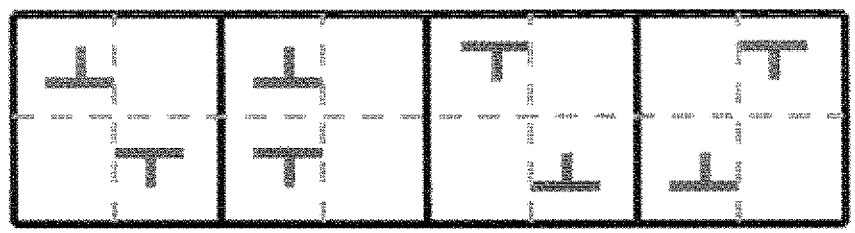
FIG. 1 is a schematic showing statistically stored dislocation structures inside of a region subdivided into even areas of two sizes represented by the solid and dashed lines.

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods.

Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel methods are therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In mapping strain in materials, there are two categories of dislocations: geometrically necessary and statistically stored. Geometrically necessary dislocations (GNDs) were first defined explicitly in 1970 by Ashby as those that contribute to the net curvature of the material. GNDs can be distributed across a grain to produce an orientation gradient or aligned to form subgrain boundaries. Statistically stored dislocations (SSDs) are those that do not contribute to the net curvature, such as dislocation loops and dipoles which have no net Burgers vector. A Burgers vector represents the magnitude and direction of the lattice distortion resulting from a dislocation in a crystal lattice.

J. F. Nye first introduced a theory for quantifying lattice curvature in terms of GNDs. Nye derived a second-rank tensor, $\alpha$, to describe the state of dislocation of a given volume of crystalline material according to the following relationship:

$$\alpha_{ij} = nb_i r_j \quad (1)$$

where r is the unit vector parallel to dislocation line, b is the Burgers vector of the given dislocation type, and n is the number of dislocations crossing a unit area normal to r. This equation can be applied to single dislocation types (unique combinations of Burgers vector and line direction) or treated as a summation of all possible types for the structure being considered in order to calculate the total state of dislocation for the region of interest.

For large volumes the Nye tensor will only account for the GNDs. However, this is only true if the SSD structures are fully contained within the measured volume. As the probe volume is decreased toward the length scale of the dislocation spacing, however, information regarding all dislocations should be accessible.

This concept is illustrated in FIG. 1, which is a schematic drawing showing statistically stored dislocation structures inside of a region subdivided into even areas of two sizes represented by the solid and dashed lines. The dislocations shown have opposite Burgers vectors so they will not contribute to lattice curvature from point to point if the large area sections are considered. If smaller subdivisions are used, however, the dislocations are seen to contribute locally, even though the alternating curvatures they induce cancel one another out over a larger length scale.

In a simple cubic structure, each term of the Nye tensor corresponds directly to a given dislocation type. For other structures, however, the densities of specific dislocation types cannot be calculated directly in this fashion because there are more than nine possible types of dislocations. Although the fact that the Nye tensor is underdetermined for most structures makes it difficult to extract the densities of specific dislocation types, it has been shown recently that for face center cubic (FCC) crystals the GND density, p, can be approximated using the following equation:

$$\rho \approx \frac{1}{b}\|\alpha\|_1 \quad (2)$$

where b is the magnitude of the Burgers vector and $\|\alpha\|_1$ is the $L_1$ norm of the corresponding Nye tensor. Using this equation the dislocation density of a material can be estimated from point to point by evaluating local fluctuations in orientation due to curvature in the crystal lattice.

In addition to dislocations, elastic strain gradients also play a role in determining the distortion of the lattice. Nye's treatment, however, ignores the presence of large-scale residual elastic strains and any contributions they make to lattice curvature. A later analysis by Kroner expands Nye's definition of the dislocation tensor by taking these effects into account. Kroner defines α in terms of the elastic distortion, β, as follows:

$$\alpha = \nabla \times \beta \quad (3)$$

The elastic distortion is calculated from the elastic strain tensor, ε, and the lattice rotation tensor, ω, according to:

$$\beta_{ij} = \epsilon_{ij} + \omega_{ij} \quad (4)$$

If elastic strain is negligible then Kroner's analysis reduces to Nye's original formulation.

The present methods disclosed herein are directed towards strain mapping of materials using either local mis-orientation mapping or Nye tensor analysis in order to produce the strain maps. In particular, the methods employed herein are directed towards the use of transmission electron microscopes in creating the strain maps. TEM has superior resolution, when compared to SEM, and it is a transmission technique that it is capable of providing images of the dislocation structure to accompany the quantitative evaluation made using the local mis-orientation mapping or Nye tensor analysis methods. This allows for a visual comparison of the resulting GND density estimate with the dislocations present in the accompanying TEM micrograph and provides useful input for the scan setup such as approximate dislocation spacing and subgrain sizes.

One approach to strain measurement in TEM is the analysis of convergent beam electron diffraction (CBED) patterns. CBED data contains a wealth of information about the structure of the material and has been used for both orientation mapping and strain analysis. However, it is difficult to acquire uniform patterns as the appearance of the patterns is highly sensitive to even small changes in specimen thickness from point to point.

An alternative to CBED is precession enhanced nanobeam diffraction. Precession enhanced nanobeam diffraction provides enhanced spatial resolution compared to selected area diffraction (SAD). The use of precession enhanced nanobeam diffraction permits quasi-kinematical diffraction conditions that make visible the reflections from the higher order Laue zones (HOLZ) that contain information about the structure parallel to the optical axis that is typically inaccessible in spot diffraction patterns.

In employing the methods of the present invention the automated crystallographic orientation mapping system for TEM (ACOM-TEM) developed by NanoMEGAS™ was used. The ACOM-TEM system rasters an electron beam across a predetermined area at a set step size on a sample inside the TEM. While rastering the system simultaneously records nanobeam diffraction patterns at each step using a high-speed camera. These off-axis patterns are then indexed against a set of computer-generated templates for the patterns from the given crystal structure(s) to create an orientation/phase map. When the scan is performed at a small enough step size then the small local shifts in orientation from pattern to pattern can be quantified and mapped in order to give a visual representation of the local strain distribution. The ACOM-TEM system provides a source of input data for dislocation density calculations because it can provide three-dimensional orientation information as well as displacement in two dimensions. Providing this input data is useful in performing Nye tensor analysis and/or local mis-orientation mapping. However, it should be understood that other TEM systems may be used provided that they can provide the necessary data for strain mapping.

After receipt of the data from the ACOM-TEM system, analysis of the data is performed using the local mis-orientation mapping method or the Nye tensor analysis method. The analyses may use the Euler angle and displacement input data from the ACOM-TEM. In performing Nye tensor analysis the best fit of the tensor is calculated by describing the contortion of the lattice for each point with respect to its nearest neighbors. Changes in the dislocation density from point to point can be measured on a nanometer length-scale. Maps produced using this method have good agreement with the dislocations visible in TEM and the values produced are in good agreement with those from literature.

Figure 2:
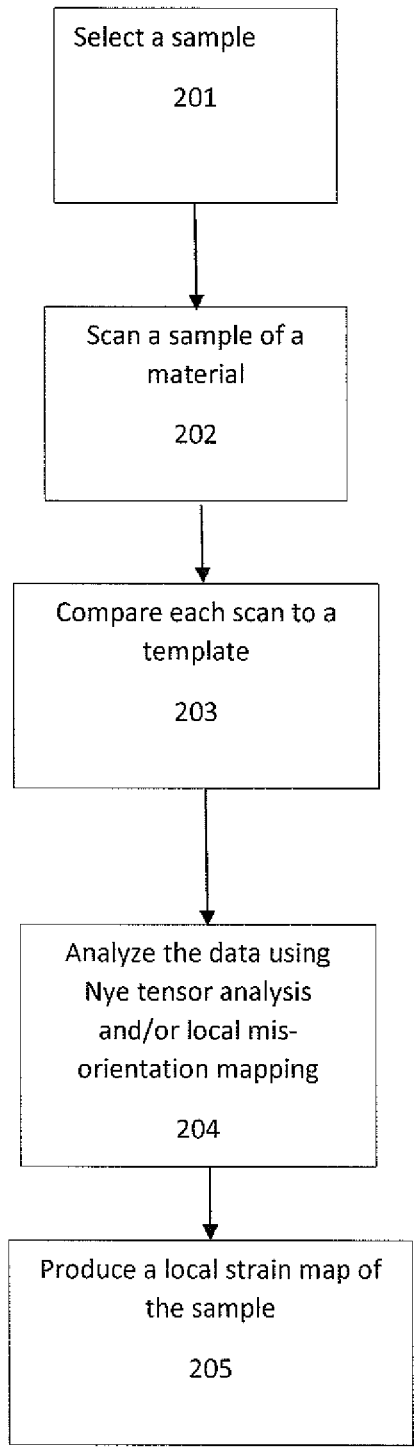
FIG. 2 is a flow chart providing an overview of the method for strain mapping a material, in accordance with an embodiment of the invention.

An overview of the method for producing a strain map is shown and described in the flow chart in FIG. 2. In step 201 a sample is selected and scanned. In general, the sample may be selected from any material that may have strain, such as metals and ceramics subject to stresses, such as heat stress, radiation, etc. The materials used in this type of analysis may be taken from vehicles, buildings, bridges and other structures where the strain impacting the material may need to be analyzed.

In step 202, the sample of material is scanned using a TEM. As discussed above a system such as the ACOM-TEM system is preferred due to its automated features. The scanning of the sample is performed over multiple steps having a step size that may be predetermined and at a beam precession angle that may also be predetermined. A beam precession angle within the range of 0-1.5° may be selected. Preferably, a beam precession angle within the range of 0.5 to 1.0° is used. A step size of 0.1-100 nm may be used, and more preferably a step size of 5 nm to 20 nm is used. For example the step size may be 20 nm by 20 nm, 10 nm by 10 nm, or 5 nm by 5 nm, or even less than these respective step sizes. In selecting the step size and the beam precession angle, preferably the volume of the sample captured in each step of the scan is small enough to ensure that it does not contain whole subgrains, but is also large enough to contain multiple dislocations in a highly plastically deformed specimen.

In step 203, each scan at a step and beam precession angle is compared to a template. The template is generated by the parameters of the material and the scanned sample. This produces data. This data is generally produced by computers that are part of the ACOM-TEM system, however the information can alternatively be produced by computers separate from the device in step 204, the data that is obtained from scanning is analyzed. The analysis that is performed may use local mis-orientation mapping or Nye tensor analysis to analyze the data. These methods are discussed in more detail below in reference to FIGS. 3 and 4 respectively. In step 205, the analyzed data is used to produce a strain map of the sample material.

Figure 3:
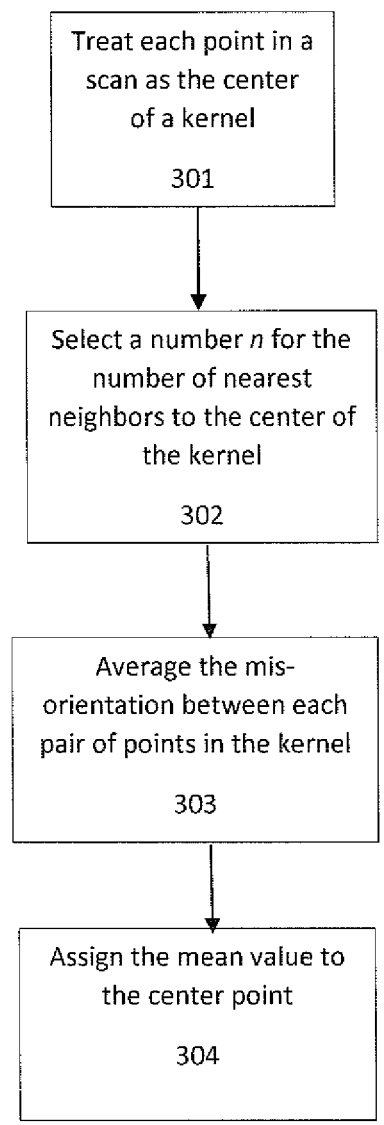
FIG. 3 is a flow chart of the local mis-orientation analysis method, in accordance with an embodiment of the invention.

FIG. 3 is a flow chart illustrating the method for performing local mis-orientation mapping. In step 301, each point in a scan step is treated as the center of a kernel of n nearest neighbors. In step 302, a number n is selected for the number of nearest neighbors to the center of kernel. The number n may be chosen from numbers from 1 to 10.

In addition to the number n an exclusion angle is chosen as part of the data analysis. The data produced by the ACOM-TEM system gives the orientation of the sample at each step. These orientations are compared to one another. Changes in orientation greater than the exclusion angle are not included in the calculation since they are caused by grain boundaries rather than dislocations. The exclusion angle may be selected from angles of 0-10°.

In step 303, the mis-orientation between each pair of points within the kernel is averaged based upon the exclusion angle. In step 304, the mean value calculated is assigned to the center point of the kernel. This calculated mean value serves as a rough approximation of GND density because any curvature within an individual grain should be accommodated by dislocations. This information is then used in step 205, discussed above with respect to FIG. 2, in order to produce a strain map of the sample.

Figure 4:
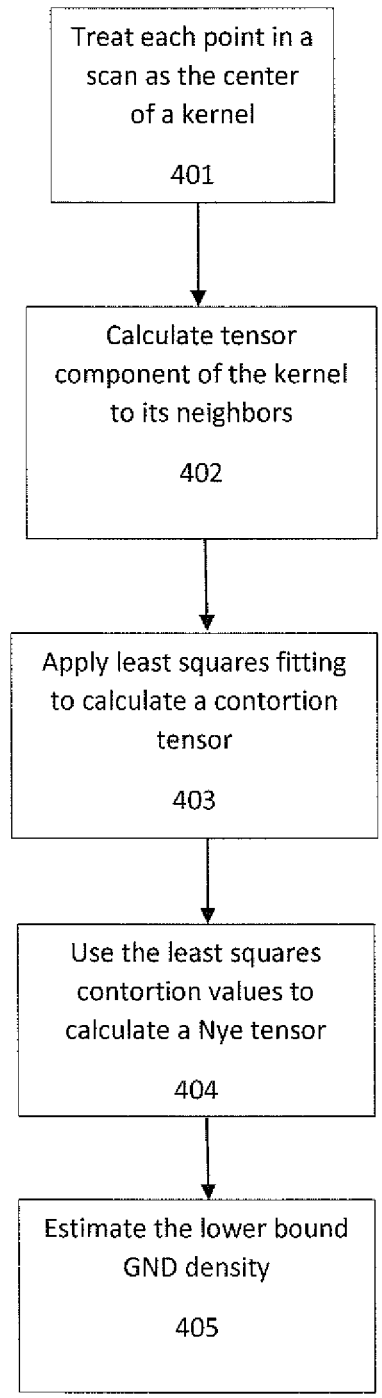
FIG. 4 is a flow chart of the Nye tensor analysis method, in accordance with an embodiment of the invention.

FIG. 4 is a flow chart illustrating the method for performing Nye tensor analysis. In step 401, each point in a scan step is treated as the center of a kernel. Each point is considered as the center of a kernel with a chosen radius. The radius may be selected from a range of one to ten neighbors. The radius defines the number of neighbors as discussed below.

In step 402 the tensor components relating the nearest neighbors in the kernel to the point are determined. In the methods described herein, eight nearest neighbors are chosen, however the number of neighbors chosen is a reflection of the selected radius. For example, a square on a grid having a radius of one means that the 4 adjacent neighbors and 4 diagonal neighbors are included, obtaining the eight neighbors. If a radius of 2 is selected the number increases to 24, etc. The tensor components are calculated based on the disorientation between the nearest neighbors. Euler angles are used as input data to calculate the disorientation axis/angle pairs. Infinitesimal rotations are assumed for the purpose of the calculation.

In step 403 a least squares fitting is applied to calculate a contortion tensor for the nearest neighbors. In step 404, the least squares contortion values are used to calculate the Nye tensor. In step 405, the equation $$\rho \approx \frac{1}{b}\|\alpha\|_1$$

is used to estimate the lower-bound GND density. In the examples discussed below the minimum resolvable GND density was $5.76 \times 10^{14}$ m$^{-2}$.

Compared to the local mis-orientation mapping method discussed above, the GND density has a direct physical interpretation in that it corresponds to an actual number of physical structures, while the local mis-orientation mapping method provides an arbitrary metric that roughly corresponds to this value.

Two examples of using methods in accordance with embodiments of the invention are provided below by analyzing the same type of material.

THE FIRST EXAMPLE

In the first example microcrystalline oxygen-free electronic copper (99.99% pure) was used to perform strain mapping within the context of twin grain boundary motion. This material was good for use due to its ability to maintain a fairly sizable dislocation density. This is due to its stacking fault energy (SFE=78 mJ/m$_2$), as well as its ability to promote twin formation.

Rolled copper plate, was purchased from McMaster Carr and cut into 1.25×1.25 cm strips. The strips were annealed for one hour at 540° C. to achieve a fully recrystallized microstructure. The strips were then rolled to a 50% reduction in order to provide a significant level of strain. The strips were subsequently annealed for 10 minutes at 400° C. to allow some recovery to occur while still leaving significant strain in the microstructure. Samples of the material were produced by mechanical polishing in order to create thin foils after being cut from the bulk specimens using an intermediate speed cutoff saw with a grinding blade. After mechanical polishing, 3 mm discs were punched from the thin foil and jet-thinned using a Struers TenuPOL-5 electropolisher.

Precession enhanced nanobeam diffraction was used in scanning the sample. An ACOM-TEM system was used and in particular the scanning was carried out in a JEOL 2100 LaB$_6$ TEM equipped with the Nanomegas SPINNING STAR™ precession electron diffraction system and ASTAR™ orientation mapping system.

In performing the scanning, the areas chosen for strain mapping were imaged prior to scanning in order to provide a reference for the features observed in the orientation and for the produced strain maps. During the scanning, precession diffraction was executed using a precession angle of 0.60° and a step size of 10.40 nm×10.40 nm, as the minimum beam spot size for this microscope was 10 nm. The diffraction patterns produced during the scanning were captured using an external high-speed camera mounted in front of the viewing screen of the microscope.

In the first example the acquired patterns were indexed automatically. "Indexing" means matching acquired patterns with simulated patterns generated by the software of the device in order to determine the orientation associated with each pattern. Following indexing the measurement parameters and crystal structure for copper were input in order to generate reference templates for diffraction spot patterns as a function of crystal orientation.

Each recorded pattern from the scanning was compared to the templates to establish the best fit. The index quality and reliability were calculated automatically using the equation:

$$Q(i) = \frac{\sum_{j=1}^{m} P(x_j, y_j) T_i(x_j, y_j)}{\sqrt{\sum_{j=1}^{m} P^2(x_j, y_j)} \sqrt{\sum_{j=1}^{m} T_i^2(x_k, y_j)}} \tag{5}$$

Where the pattern is represented by the intensity function $P(x,y)$, while every template i is given by the function $T_i(x,y)$, the highest Q value corresponds to the solution, and the equation:

$$R = 100\left(1 - \frac{Q_2}{Q_1}\right) \tag{6}$$

where R is the index. The index is the absolute quality of the matching between the template and captured pattern and the reliability is a comparison of the best index with the next best index.

The index quality and reliability values were assessed to ensure that the scan was of good quality and that each point had been accurately matched against all possible orientations. The threshold values chosen for good quality were a minimum index of 300 and a minimum reliability of 20 within grains—reliability at boundaries tends to drop toward zero. Reliability is a metric that compares the index of the two best possibilities in order to ensure there is no ambiguity.

Acquired data was then exported to an .ANG file format compatible with the TSL OIM Analysis software package developed by EDAX. Using this software, maps of the local orientation spread within a three pixel radius around each individual pixel of the orientation map were generated.

The resolution of this method is limited by the electron beam spot size. The spot size may range from <1 nm to 100 nm and scan step sizes may be chosen to capture the diffraction patterns. The chosen step size translates to the pixel size. Thus, if the spot size used is larger than the step size, then each pixel will contain information from the orientation of overlapping areas.

In the first example, local mis-orientation mapping was performed as discussed above in relation to FIG. 3. In this example, a kernel size of n=3 and an exclusion angle of 5° was chosen for all data for the purpose of consistency.

Local mis-orientation mapping serves as a rough approximation of GND density because any curvature within an individual grain should be accommodated by dislocations. After performing the analysis a strain map of the sample was produced.

THE SECOND EXAMPLE

Another example of the method was also performed using microcrystalline oxygen-free electronic copper (99.99% pure). Rolled copper plate purchased from McMaster Can was cut into 1.25×1.25 cm strips and annealed for one hour at 540° C. to achieve a fully recrystallized microstructure. The strips were then subjected to various rolling reductions ranging from 5 to 50 percent in order to achieve a range of dislocation densities.

Samples of the material were prepared by cutting the copper perpendicular to the rolling direction. The copper was then mechanically thinned to approximately 100 μm. 3 mm discs were punched from the thinned sections and jet polished using a Struers TenuPol-5 electropolisher. Additionally, in this example lift outs of individual boundaries were prepared using an FEI Strata DB235 focused ion beam (FIB).

Scanning was then performed and data acquired using a JEOL 2100 LaB$_6$ TEM, NanoMEGAS SPINNING STAR™ precession electron diffraction and the ASTAR™ ACOM-TEM systems. The ACOM-TEM systems were used to acquire the orientation data used as the input for GND density calculations. A precession angle of 0.60° was utilized for all scans. Step sizes of 10.40 nm for both of the x and y directions were used. The beam spot size used was 10 nm. The patterns were acquired and indexed automatically.

The orientation data for this example was also analyzed using the TSL OIM Analysis software package developed by EDAX. As discussed above with respect to the first example, using this software, maps of local orientation spread were generated in order to visualize internal strains due to lattice curvature.

In order to obtain a more accurate, quantitative estimate of the GND density than the local mis-orientation analysis method discussed in relation to FIG. 3 and used in example 1, the Nye tensor analysis method was used, as discussed above in relation to FIG. 4. In using the Nye tensor analysis method the contortion tensors relating each point to its eight nearest neighbors were calculated. Each point was considered as the center of a kernel with a radius of one neighbor and the tensor components relating the eight neighbors in the kernel to the kernel were determined. A least-squares fitting was then applied to calculate a single contortion tensor that best described the relationship between the center point and its neighbors. These least-squares contortion values were then used to calculate a single Nye tensor that describes the state of dislocation at each point. The equation $$\rho \approx \frac{1}{b}\|\alpha\|_1$$

was then used to estimate the lower-bound GND density based on the assumption that all dislocations have a ½<110> Burgers vector since Cu is FCC. For other crystal structures where only a single family of Burgers vectors are present (such as ½<111> in body-center cubic crystal structure), this assumption is easily adapted. For crystal structures with more than one family of dislocations, such as HCP Hexagoanl close packed crystal structure, a weighted average Burgers vector must be calculated.

Only five of the nine tensor components were directly accessible from the data, therefore only those components were taken into consideration. Contour plots of the estimated lower-bound GND density were generated in origin for direct comparison and cross-referencing with the TEM micrographs of the analyzed region. This was then used to produce a strain map of the sample.

Analysis

The strain maps produced using the local mis-orientation and Nye tensor analysis methods described herein show a good correlation with the expected strain distributions around microstructural features.

The local mis-orientation method was able to measure small changes in orientation, from a fraction of a degree to 2.5°, although larger deviations are detectable if they are present, due to elastic and plastic strain within individual grains with a resolution of 10 nm² while capturing an area of ~7 µm². The scan area is theoretically limited only by the size of the thinned area of the sample being investigated. The scan size chosen in examples 1 and 2 was chosen because it matches well with the magnification required to view the features of interest in these samples.

Figure 5A:
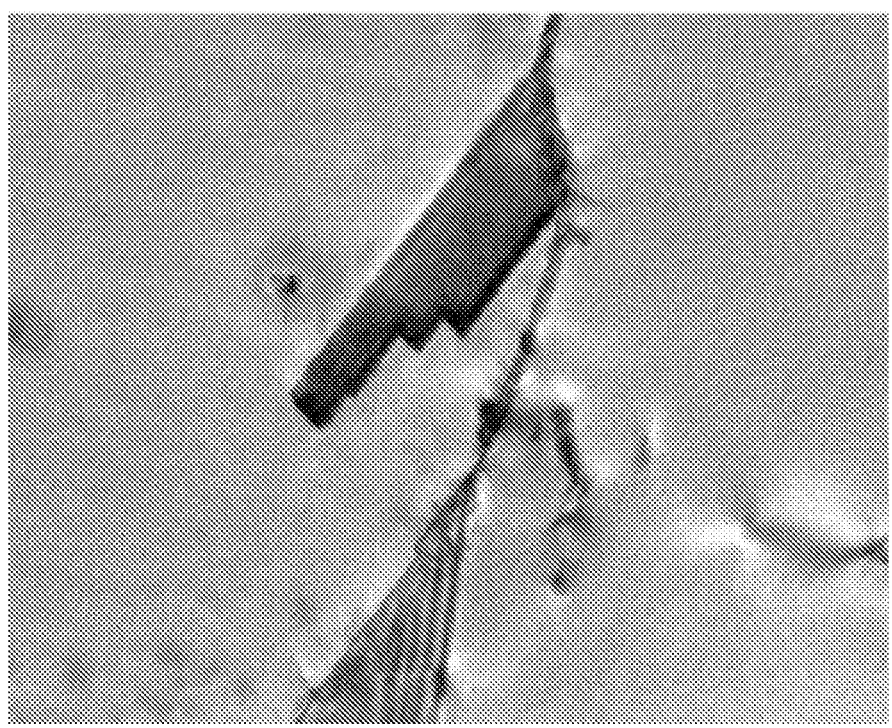
FIG. 5A is a TEM micrograph of a scan area.
Figure 5B:
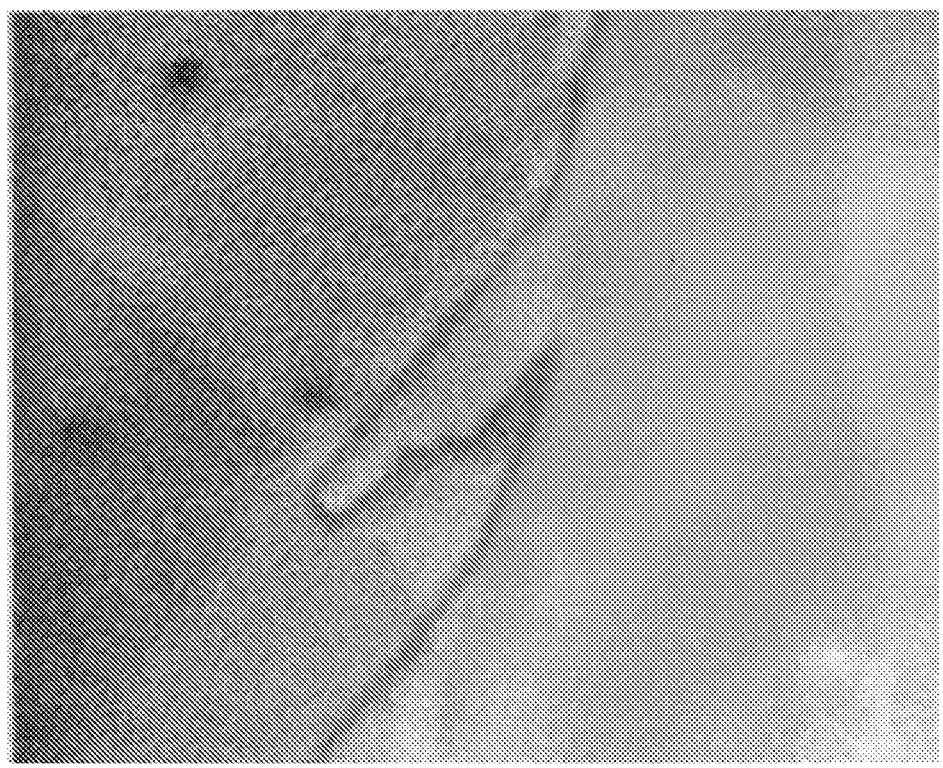
FIG. 5B is a grayscale index quality map, where light is high quality.
Figure 5C:
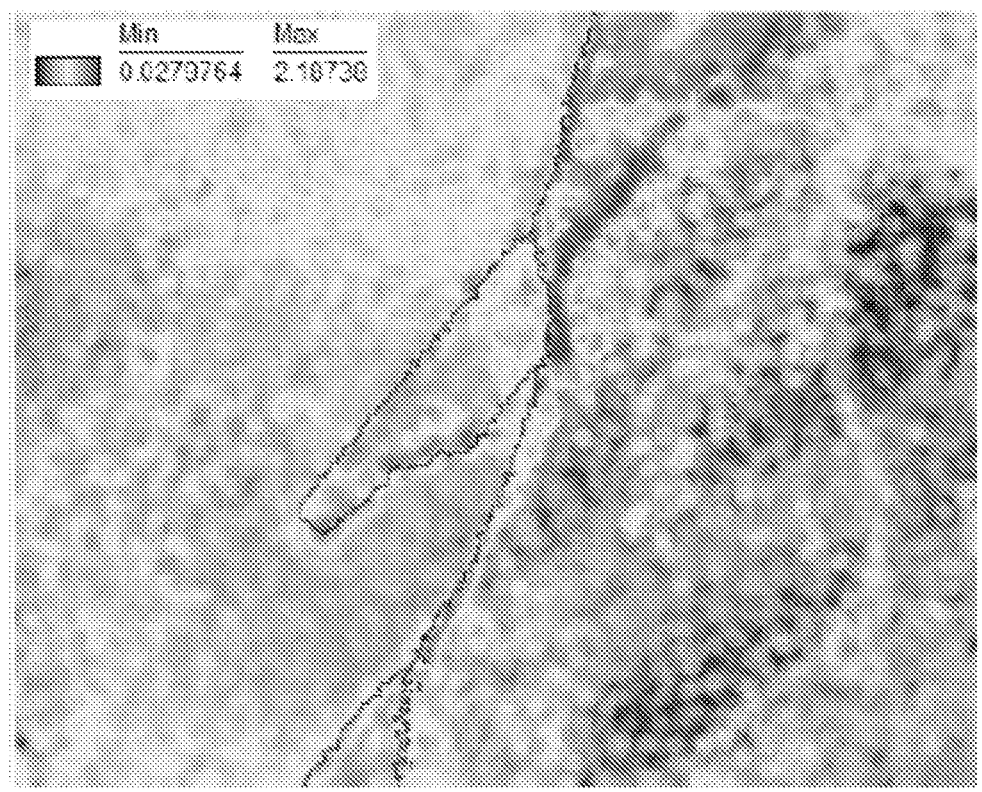
FIG. 5C is a local orientation spread map showing point to point changes in orientation within grains.

FIGS. 5A-5C show an area with a feature of interest, in this case a faceted twin domain protruding from a high angle boundary, as well as the corresponding inverse pole figure (IPF) orientation map generated using ASTAR and a map indicating the quality of the index for that orientation map. The local spread of orientations around each pixel of the orientation map is shown in FIG. 5C. The key in FIG. 5C in the upper left hand corner of the image is in degrees of disorientation. This is analogous to strain because it shows the deformation of the lattice inside individual grains both with and without the visible presence of dislocations.

Figure 6A:
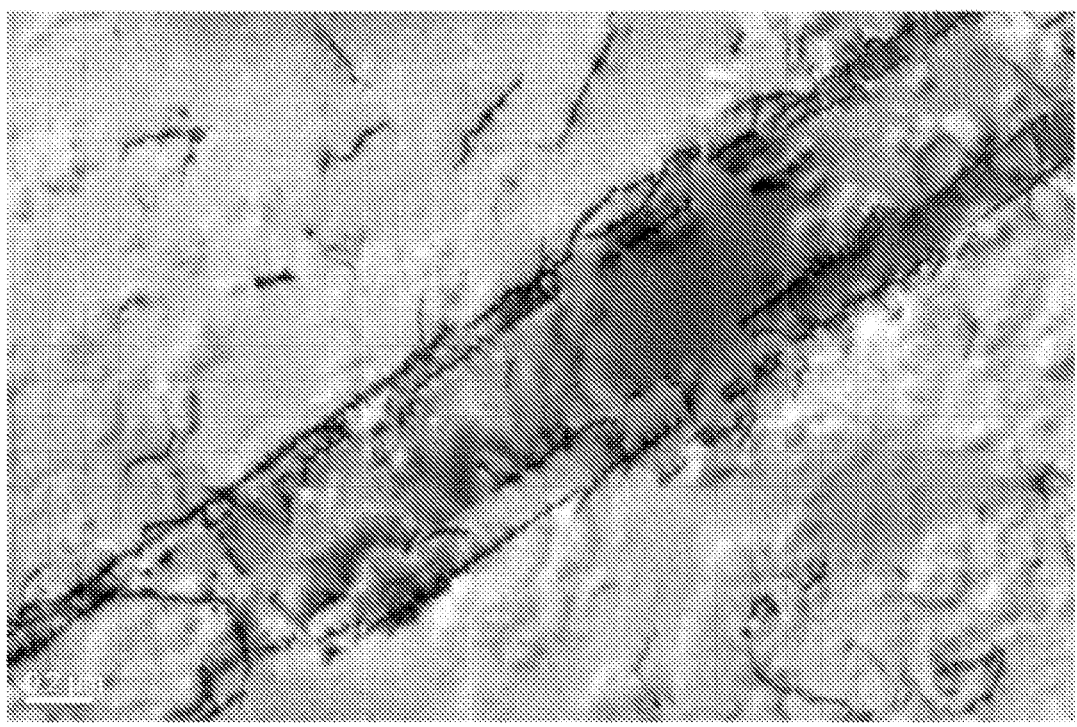
FIG. 6A is a TEM micrograph of a scanned area.
Figure 6B:
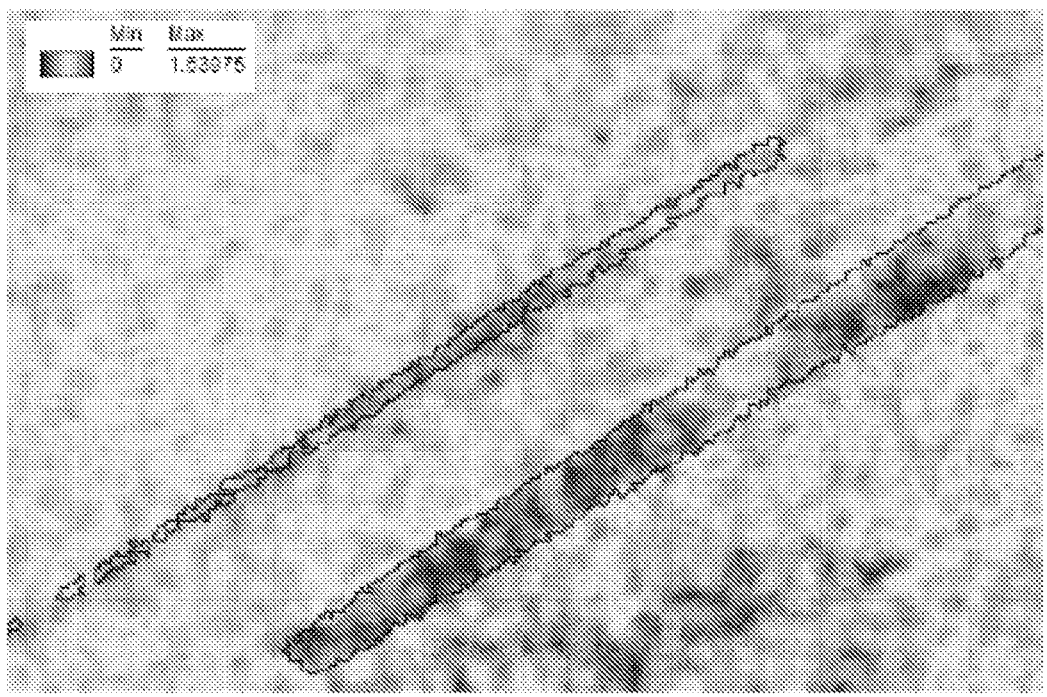
FIG. 6B is a local orientation spread map of the scanned area shown in FIG. 4A.
Figure 6C:
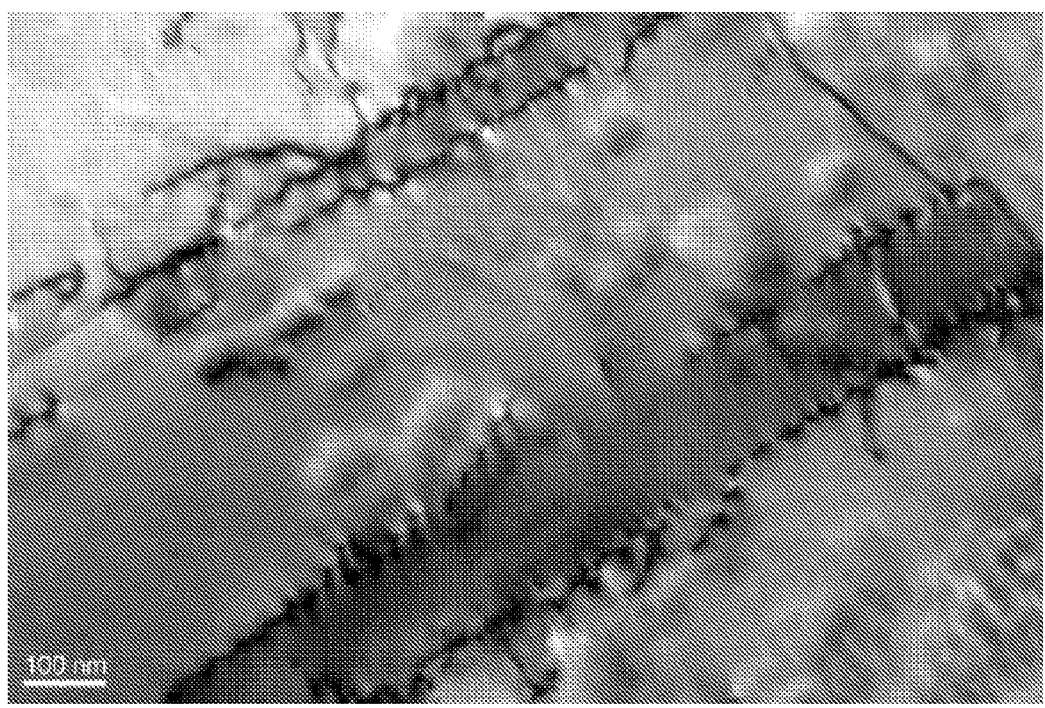
FIG. 6C shows the strained region shown in FIG. 4B at higher magnification.
Figure 7A:
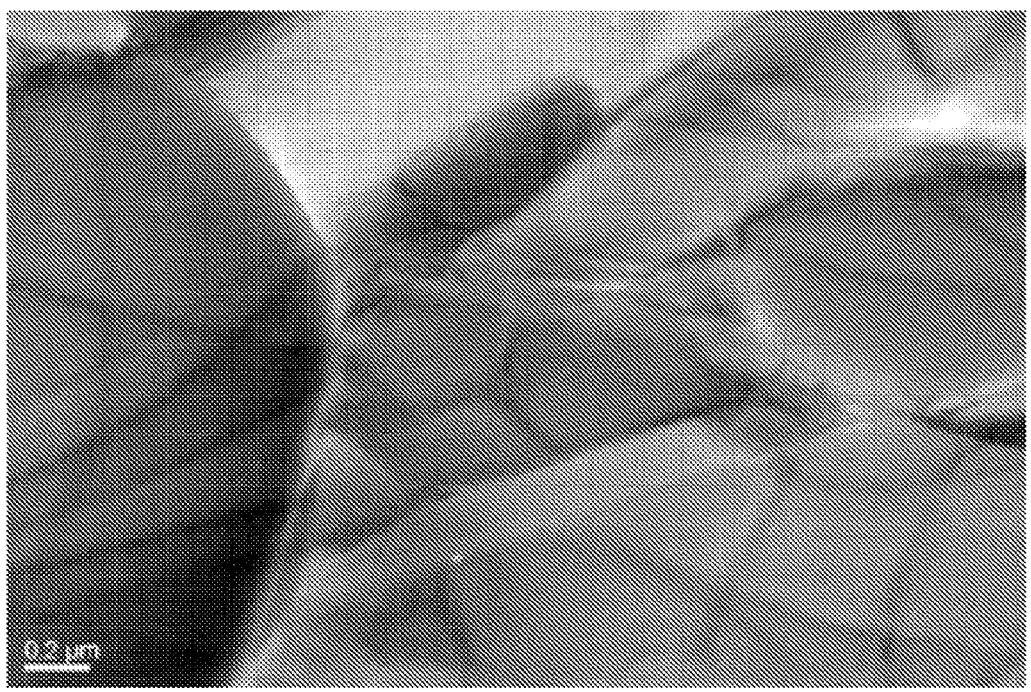
FIG. 7A shows a TEM micrograph of a scanned area.
Figure 7B:
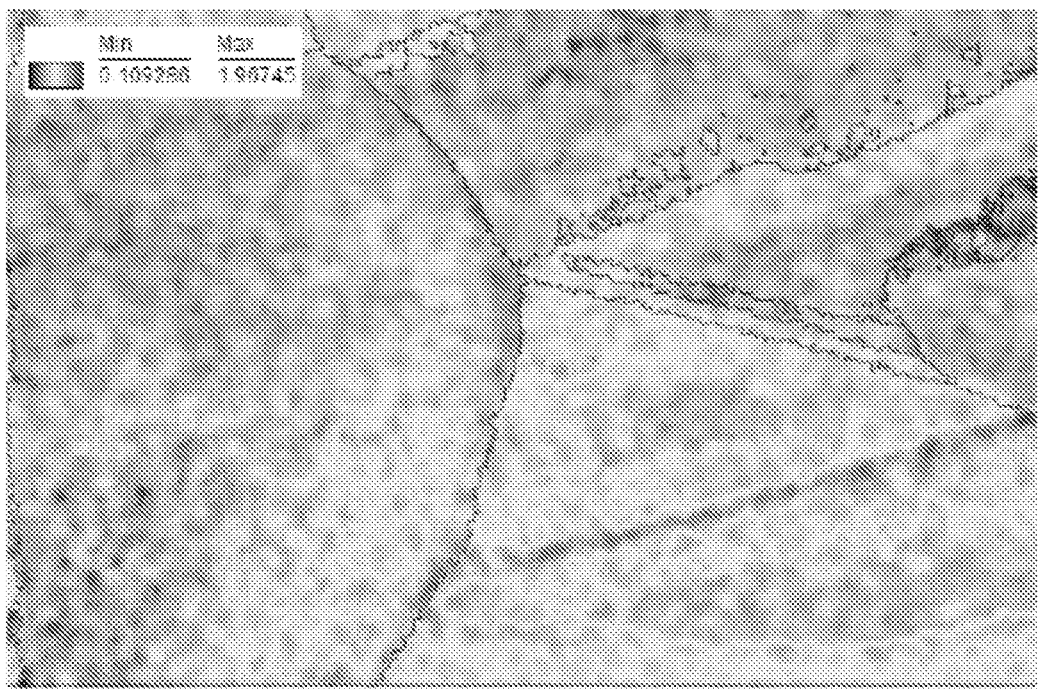
FIG. 7B is a local orientation spread map of the area shown in FIG. 5A.
Figure 8A:
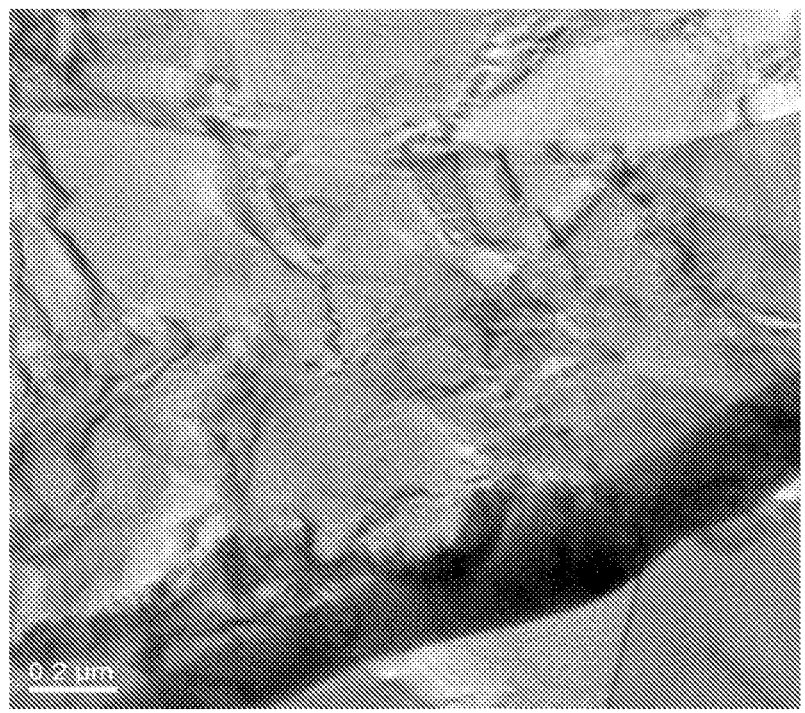
FIG. 8A shows a TEM micrograph of triple junction and LAGB, 6A-6D.
Figure 8B:
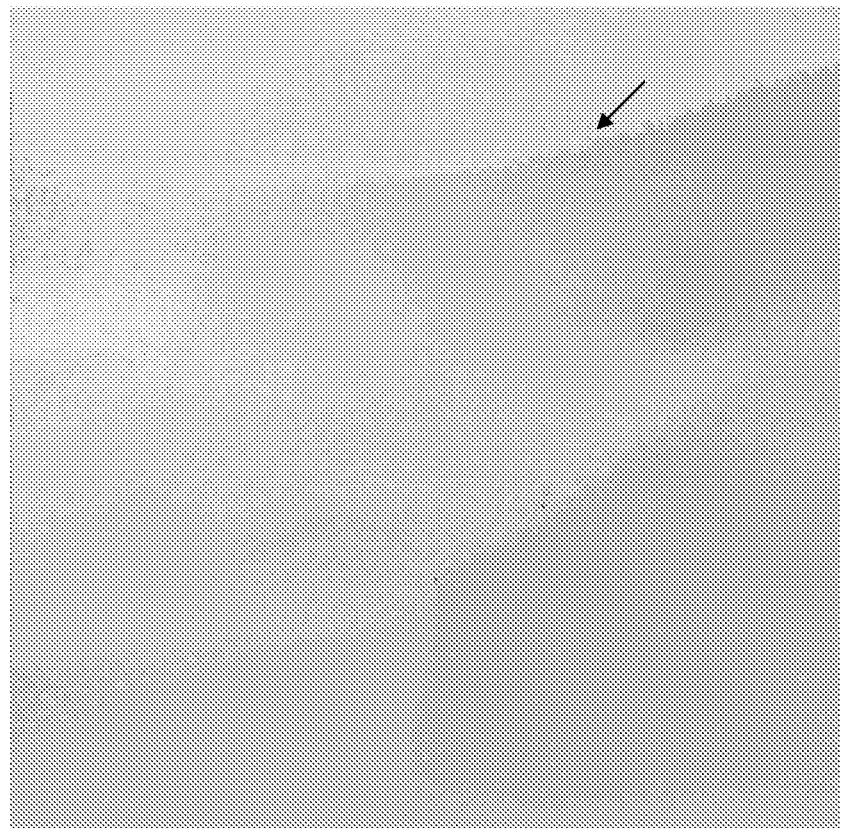
FIG. 8B shows corresponding inverse pole figure map of FIG. 6A.
Figure 8C:
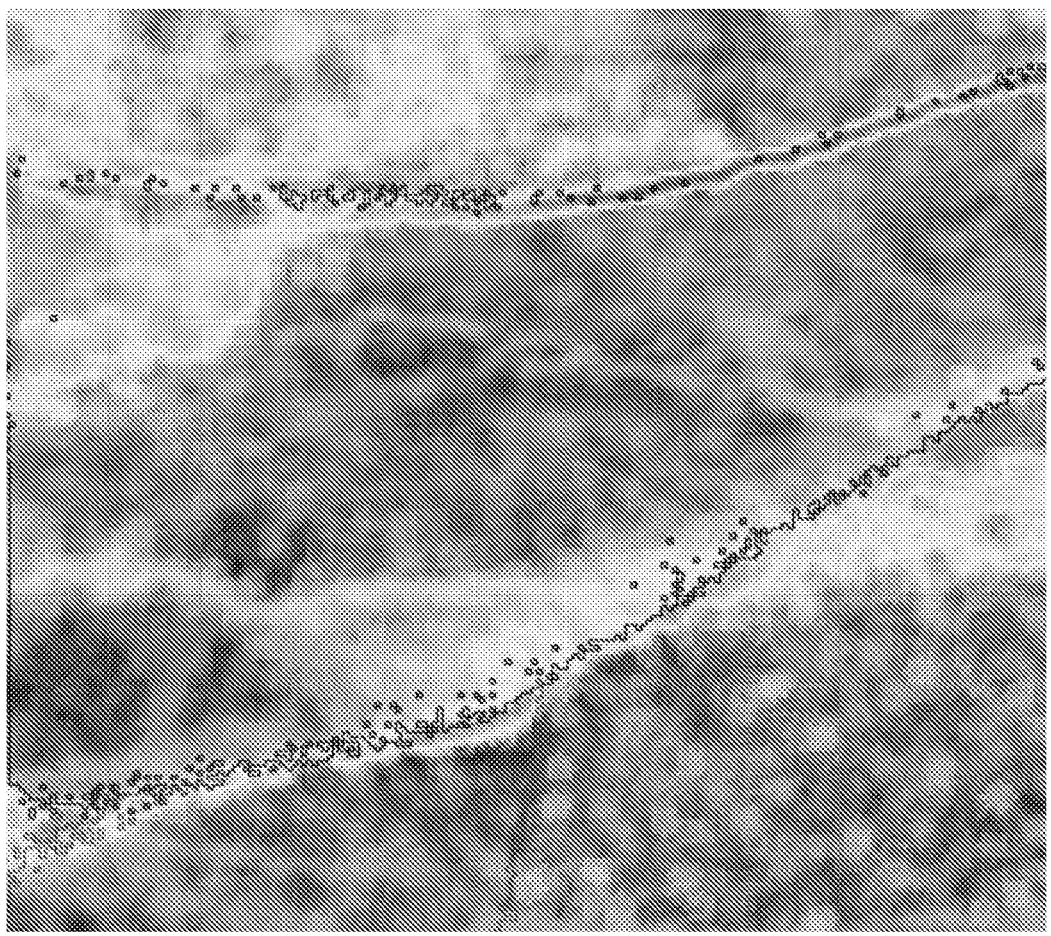
FIG. 8C shows the local orientation spread ($3n$).
Figure 8D:
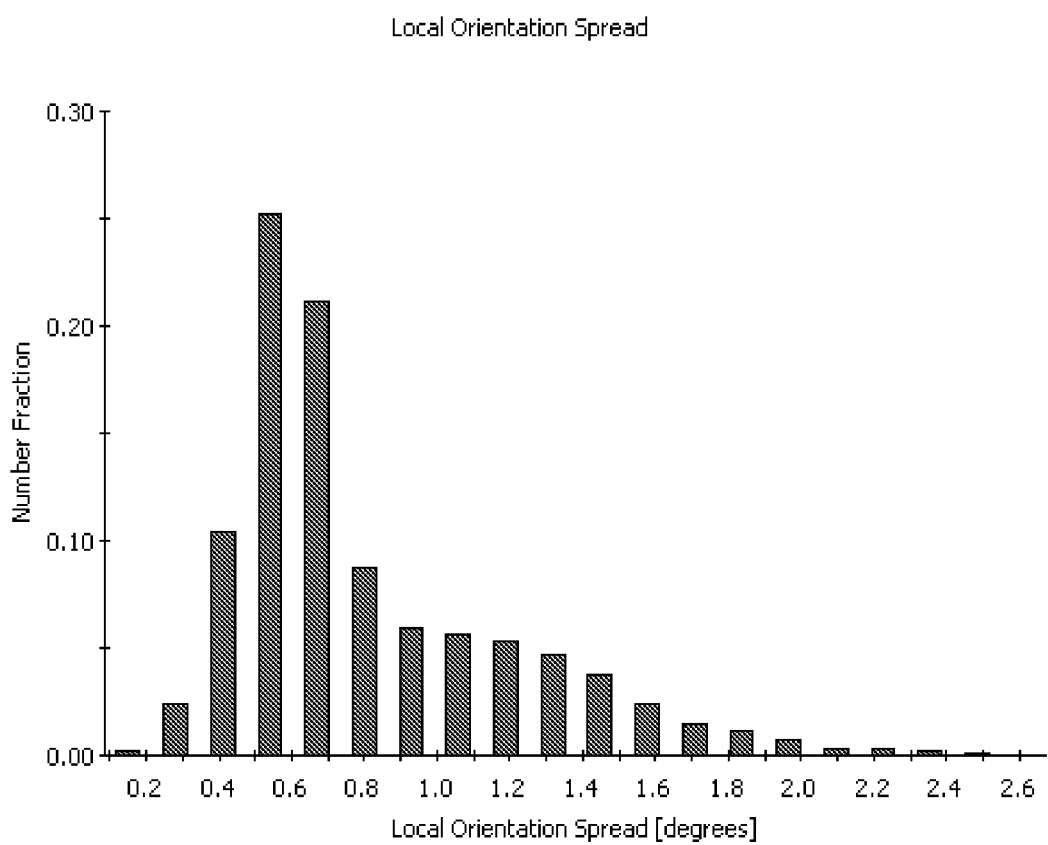
FIG. 8D shows the number fraction distribution of the local orientation spread.

FIGS. 6A-6C and FIGS. 7A-7B show two twinned regions of samples and the corresponding strain maps for those samples. Each case shows regions of high strain concentrated around different microstructural features. In FIGS. 5A-5C discussed above the region of highest strain appears to be free of dislocations, indicating purely elastic strain, whereas the highest strain concentration in FIGS. 6A-6C is in a region where several dislocations are present, as can be seen in FIG. 6C. The region of highest strain in FIGS. 7A-7B is along a subgrain boundary.

For example 2 the analysis of the data was performed using the Nye tensor analysis method.

The Nye tensor used in the Nye tensor analysis method can be described in terms of the contortion K as follows:

$$\alpha_{ij} = K_{ji} - \delta_{ij} K_{kk} \quad (7)$$

Where $K_{kk}$ is in the Einstein summation notation implying that $K_{kk} = \Sigma_i K_{ii} \cdot \delta_{ij} = 1$ for $i=j$ and $\delta_{ij}=0$ for $i \neq j$. Nye defined the contortion as a second-rank tensor:

$$K_{ij} = \frac{\partial \varphi_i}{\partial x_j} \approx \frac{\Delta \varphi_i}{\Delta x_j} \quad (8)$$

$\partial \varphi_i$ is the three-dimensional rotation vector and $\partial x_j$ is the displacement vector. These values can be found experimentally using the ACOM-TEM system and as such are the inputs. First, the axis-angle pair for the disorientation between each point and its neighbors is calculated. Then the rotation vector $\partial \varphi_i$ is approximated as the product of the axis and angle according to infinitesimal rotation theory. $\partial x_j$ is the displacement between the steps being compared. Equation 8 is undefined whenever j=3 because the displacement along the z-axis is zero. These undefined values for $K_{i3}$ will carry through when K is plugged into equation 7. Equation 7 can be written explicitly as:

$$\alpha_{ij} = \begin{pmatrix} -K_{22} - K_{33} & K_{21} & K_{31} \\ K_{12} & -K_{11} - K_{33} & K_{32} \\ K_{13} & K_{23} & -K_{11} - K_{22} \end{pmatrix} \quad (9)$$

From this expression it is clear that the components $\alpha_{11}$, $\alpha_{22}$, $\alpha_{31}$, and $\alpha_{32}$ will be undefined with the present inputs.

For example 2, maps of local orientation spread were produced as a preliminary method for assessing strain using ACOM-TEM data. The maps provided a rough estimate of the strain in the lattice because any local changes in the crystal orientation are caused by the presence of dislocations or long-range elastic strain gradients.

An example of a local spread map is shown in FIGS. 8A-8D along with a corresponding TEM micrograph and orientation map. The local spread maps are normalized to the minimum and maximum orientation spread values present within the dataset with high angle grain boundaries (HAGBs), Σ3 boundaries, and low angle grain boundaries (LAGBs, 2-15°).

At this magnification it is possible to resolve the width of the boundary as a result of which the orientation does not jump from one point in the scan to the next but can be seen as a gradient across a finite distance. As a result the TSL software fails to identify the 7° LAGB indicated with the solid arrow in FIG. 8B despite its clear presence. Instead the boundary is resolved as a buildup of small point-to-point mis-orientations that result from the array of GNDs of which it consists. This results in a tail to the right on the spread distribution which is typically Gaussian when LAGBs are not present. It is important to note that while some of the strain concentrations in the local spread map such as the ones that are readily visible in the TEM micrograph, are resolved others will not be resolved. This helps to demonstrate the importance of characterization of the dislocation content beyond imaging. In addition, the effects of bend contours are not seen in the local spread, reducing the level of noise in the image.

Figure 9A:
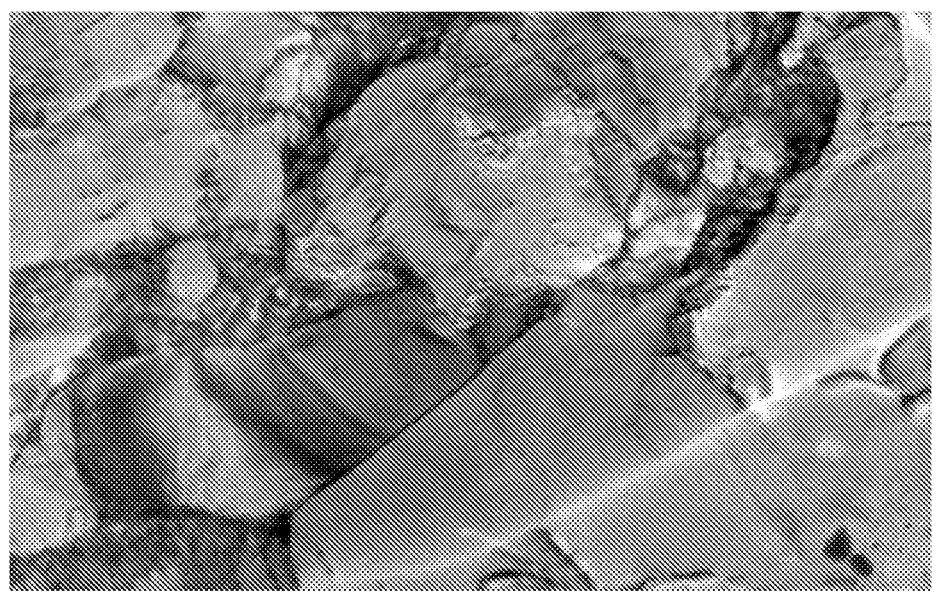
FIG. 9A shows a TEM micrograph of a HAGB in a region that has undergone a partial recovery process.
Figure 9B:
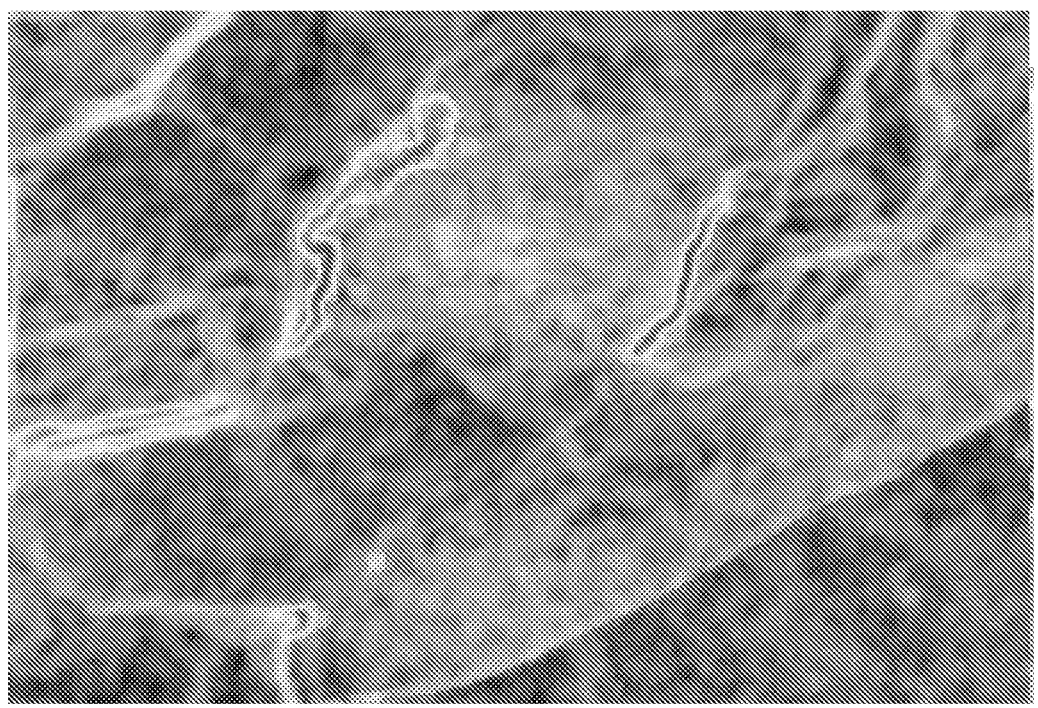
FIG. 9B shows a local orientation spread map produced for the region shown in FIG. 9A.
Figure 9C:
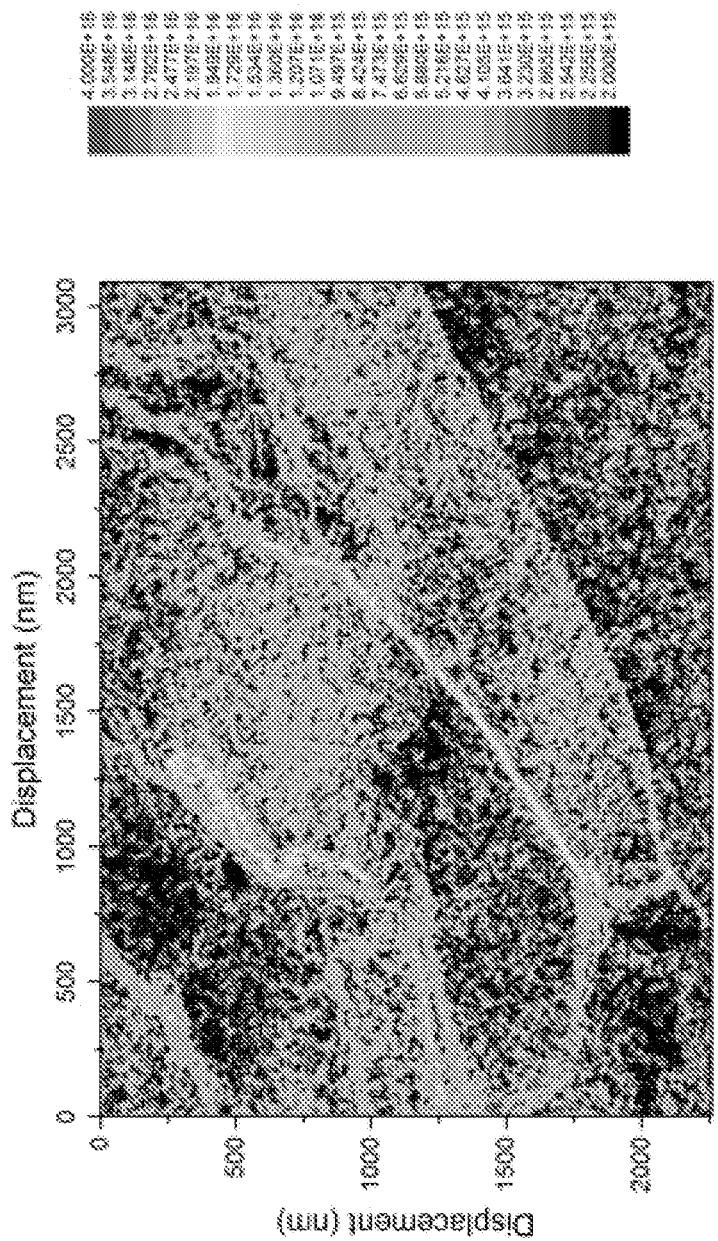
FIG. 9C shows the estimated lower-bound GND density map.

A more quantitative visual understanding of the GND structure is provided by the lower-bound GND density maps. By calculating the defect population directly, the results can be more easily compared to models and a more exact estimate of the stored energy can be produced. FIGS. 9A-9C show a partially recovered region near a HAGB with the corresponding local spread and lower-bound GND density maps. The local spread and GND density maps are qualitatively similar, but the GND density map better describes the sub-grain boundaries present in the region, especially in the region marked with an arrow. In addition, the GND density map has the advantage of being more readily interpretable, as the colors correspond directly with the number of defects present, whereas the local spread provides a relative comparison.

The GND density is plotted on a log scale in order to show the full range of values. The values calculated using the present method are high compared to those reported in the literature from EBSD data, which tend to range from $10^{13}$-$10^{16}$ m$^{-2}$. This can partially be explained by the regions being examined. GND mapping in EBSD typically shows the highest densities in the regions along the boundaries, with low densities in the grain interiors. In this example regions directly adjacent to grain boundaries are examined Another factor that contributes to the high GND density values reported herein is the minimum angular resolution of the indexing software used to determine the orientation at each point. The minimum resolution for the current indexing method is approximately 0.5°. Any rotation that is smaller than this value but still detected by the software will be inflated to this minimum, artificially increasing the densities reported Improvements to the angular resolution of pattern indexing will reduce the significance of this effect.

The step size used for the acquisition of orientation data is more than an order of magnitude beneath the minimum dislocation cell size for copper of ~400 nm, both as predicted by models and observed in literature. As a result, this technique ought to be able to resolve the walls and interiors of dislocation cells, even in metals that have undergone severe plastic deformation, as shown in FIG. 9C. In fact, the step sizes used are on the same order of magnitude as the dislocation spacing. As a result of this, it is probable that the measured volumes include fractions of defect structures that, taken together, would be considered as SSDs. If the complete SSD structure is not contained within the volume used for the calculation of the Nye tensor, then those dislocations will be taken into consideration since their Burgers vectors contribute to the local curvature even though they are cancelled out if a larger volume is considered. As a result, although the values reported herein are referred to as GNDs, they ought to represent a larger fraction of the total dislocation density than GND densities calculated using larger probe volumes. In FIG. 9C the dislocation cell walls are clearly outlined, as expected, but variations in dislocation density within the interiors of the individual cells due to SSDs are also resolved.

It is important to note that if a high GND density is reported where it is clear that none is present then the curvature in the lattice at that point must be due to elastic strain. Elastic strain cannot be measured using the current approach, although it can be extracted from an on-axis nanobeam diffraction pattern by cross-correlation with a reference pattern from an unstrained region. If significant elastic strains are present they will also contribute to the inflation of GND density values for the present methodology since they are not taken into consideration in the calculation so all orientation changes are attributed to dislocations.

A difficulty with the present analysis is the unknown thickness of the specimen along the z-axis, which is similar to the difficulties encountered with EBSD being a surface technique. This results in only five of the components of the Nye tensor being directly accessible. This problem can be addressed computationally with additional assumptions. However, an embodiment of the present invention is directed to applying Nye's plasticity model to the data acquired by precession-enhanced ACOM-TEM.

Figure 10A:
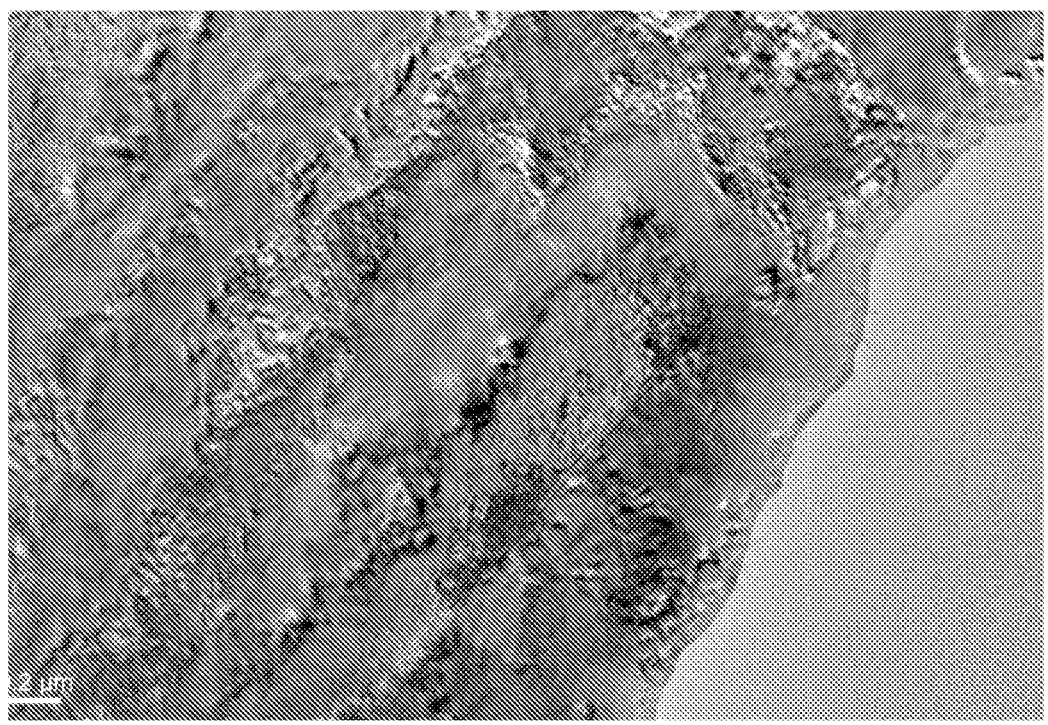
FIGS. 10A and 10B show TEM micrographs of the scan area, where
Figure 10B:
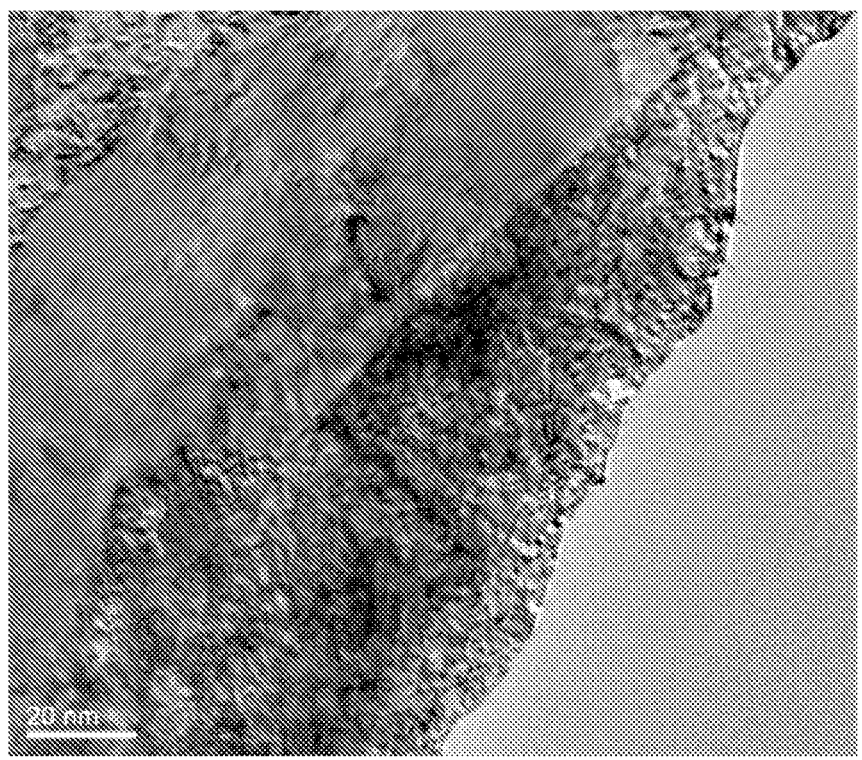
Figure 10C:
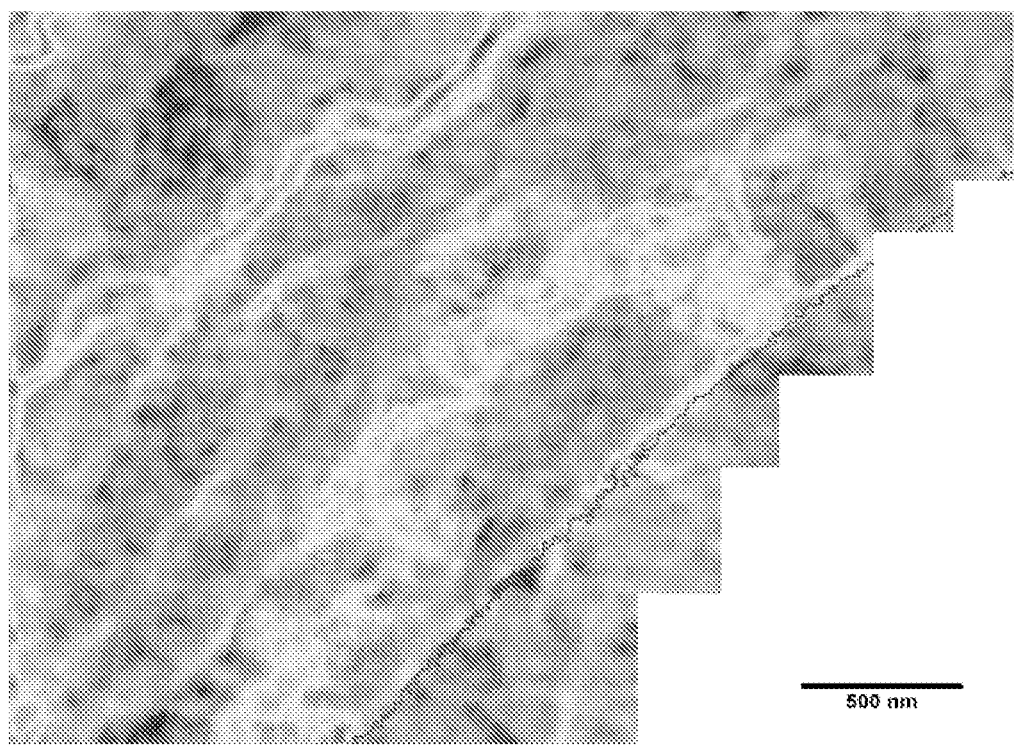
FIG. 10C shows a local orientation spread maps corresponding to the region shown in FIG. 10A with a step size of 10.4 nm.
Figure 10D:
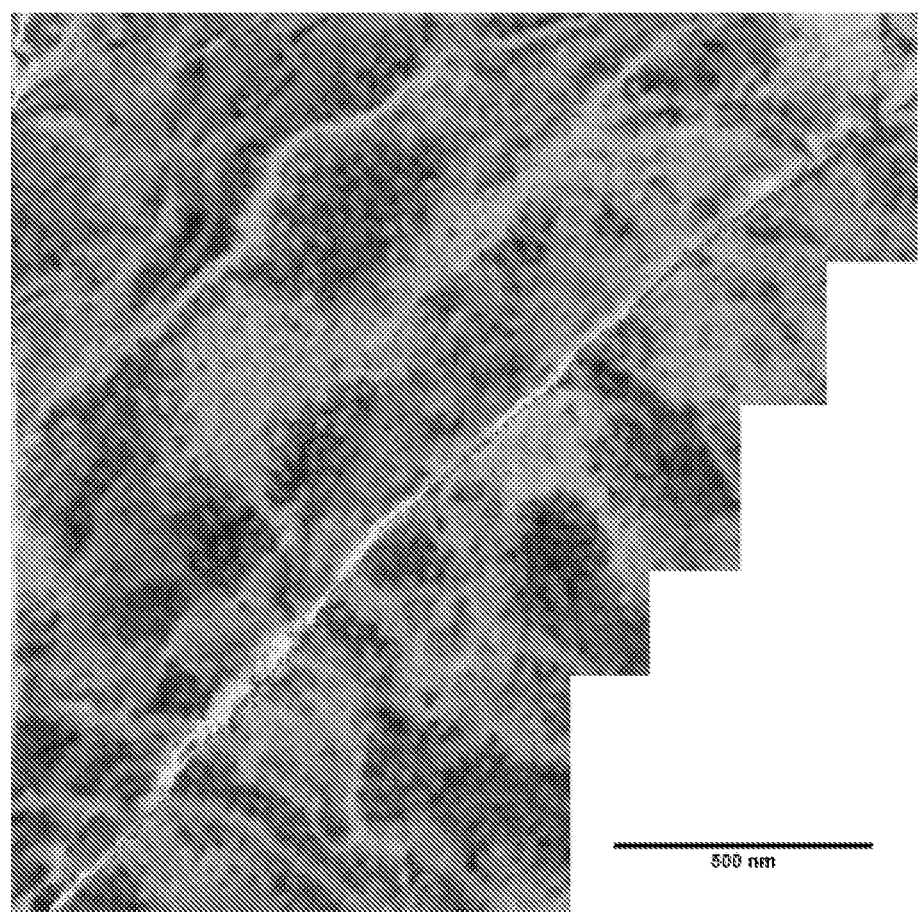
FIG. 10D shows a local orientation spread map corresponding to the region shown in FIG. 8B with step sizes of 3.9 nm.
Figure 10E:
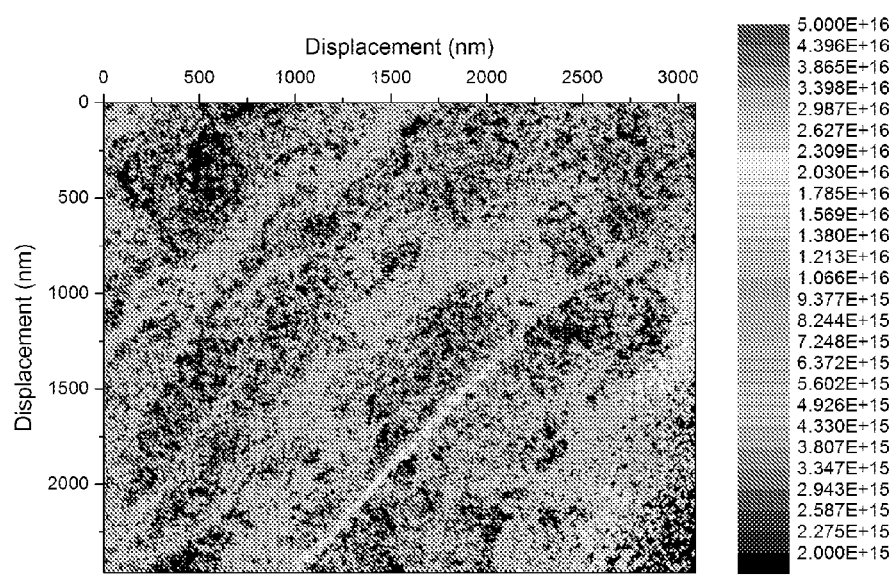
FIG. 10E shows a maps of estimated lower-bound GND density produced from the same data as used for producing the map shown in FIG. 10C.
Figure 10F:
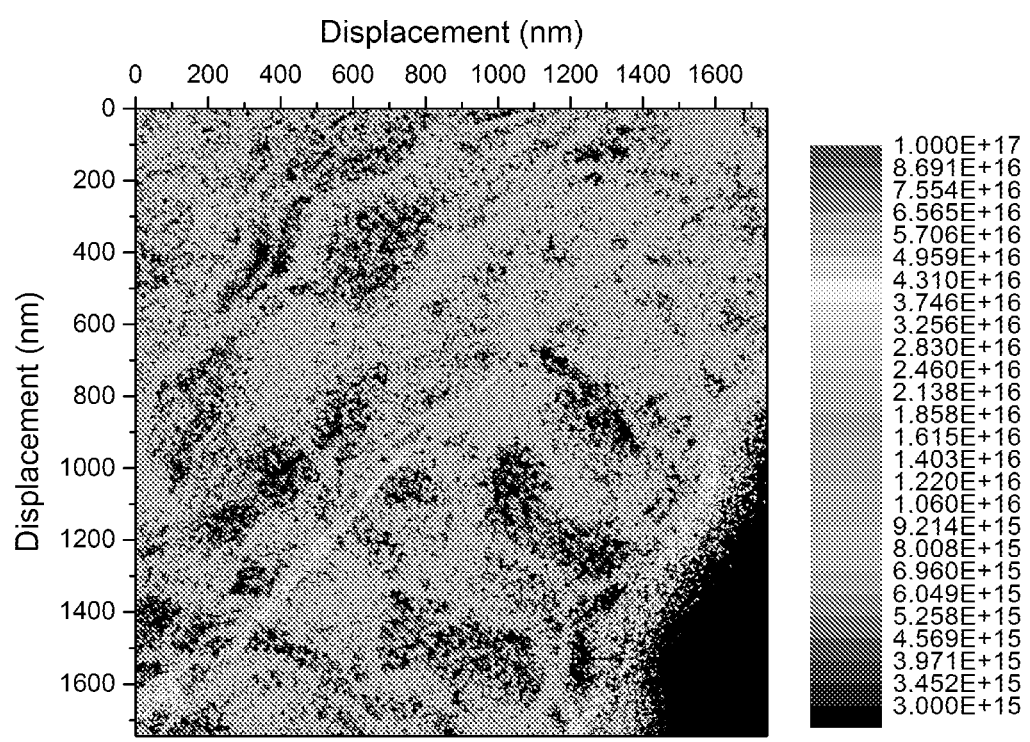
FIG. 10F shows a maps of estimated lower-bound GND density produced from the same data as used for producing the map shown in FIG. 10D.
Figure 10G:
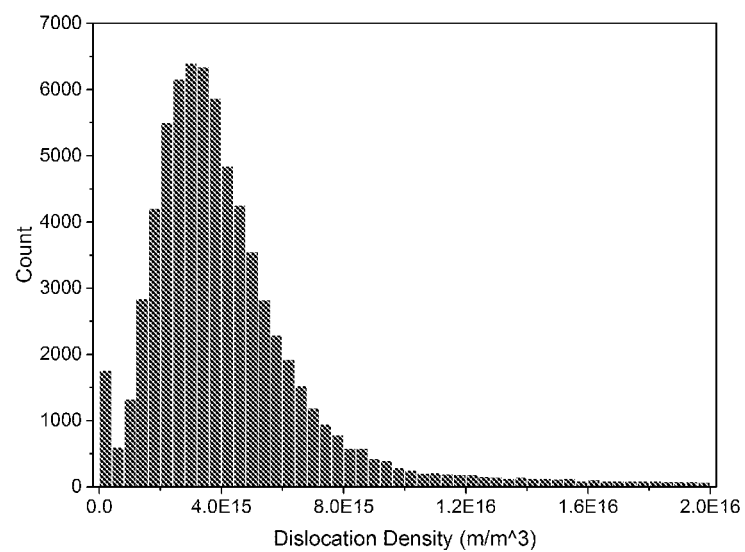
FIG. 10G is a histogram showing the distribution of GND densities present in FIG. 10E.
Figure 10H:
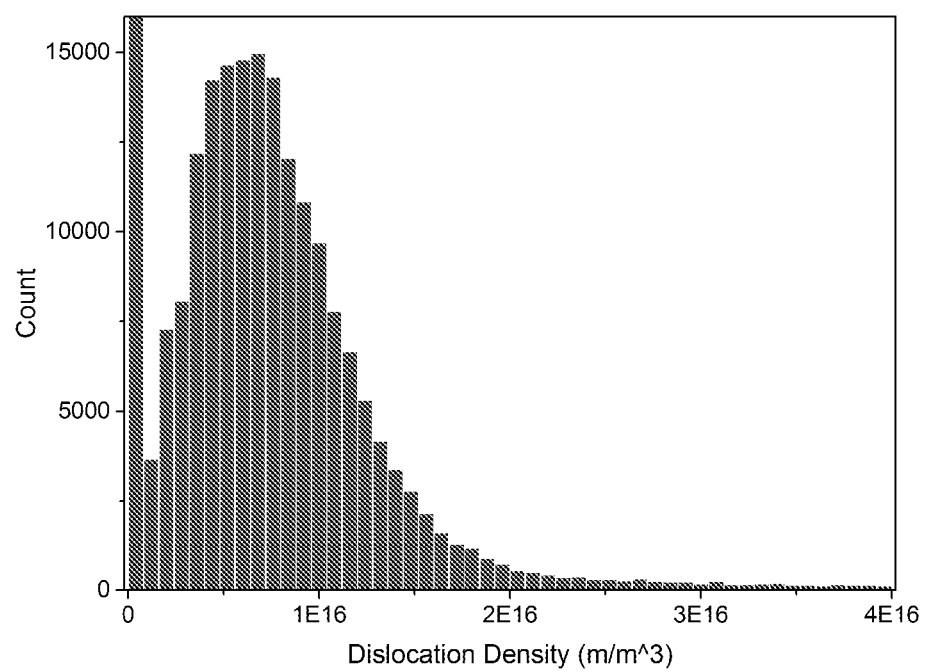
FIG. 10H is a histogram showing the distribution of GND densities present in in FIG. 10F.

In example 2, a step size of 10.4 nm was chosen because it matches well with the minimum probe size of the TEM being used. However, because the defect spacing and feature size is on the same order of magnitude, a smaller step size of 3.9 nm was used for comparison. As can be seen in FIGS. 10A-10H decreasing the step size results in an increased spatial resolution. The resulting maps reveal the GND structure in greater detail, removing much of the noise present in the maps produced with the larger step size. Despite these differences, the overall distribution of densities reported remains approximately the same as can be seen in FIGS. 10G and 10H. The step size for acquisition can be further reduced, potentially down to a fraction of a nanometer. Doing so without also reducing the probe size of the TEM will result in over-sampling, with each pattern containing much the same information as the patterns acquired adjacent to it. Decreasing the step size is also a trade-off in terms of acquisition time for a scan of the same area since a scan with a smaller step size will contain many more data points.

Two methods for quantitatively mapping strain using ACOM-TEM data have been demonstrated—local mis-orientation mapping and Nye tensor mapping.

Local mis-orientation mapping used in example 1 has been developed for visualization of local strain distributions over large regions of polycrystalline TEM samples without the need for high resolution images or an unstrained reference area. Local mis-orienation mapping can be used to assist in studies of microstructural evolution and to better characterize materials on the nanoscale. Local mis-orientation mapping is accurate and gives a good visual representation, although it is not truly quantitative. Increased accuracy and resolution may be achieved using this method in a microscope capable of achieving a smaller minimum spot size in nanobeam mode.

The local mis-orientation mapping used in example 1 provides relative values of strain from point to point for a given region. The values can be compared directly from sample to sample for a given material and consistent acquisition parameters. This method is applicable to all known crystal structures as long as their diffraction patterns can be indexed accurately.

The Nye tensor analysis and the estimated lower-bound GND density approach provides an approximate measurement of the dislocation density at a given point. These values are directly comparable to one another because they are a measurement of the number of defects present. This method is easily adapted to BCC materials and other structures that contain only a single family of dislocations. It can be adapted to other crystal structures through the calculation of a weighted Burgers vector that describes the all the dislocation types present and their relative frequency.

Due to the short length-scale of the measurements described herein, the dislocation densities reported ought to take into account some fraction of the SSDs present as well as the GNDs.

Increased accuracy for both methods described herein can be achieved by the improvement of the indexing for the diffraction patterns in order to increase angular resolution. Likewise, improved spatial resolution can be achieved using a finer probe and step size.

The effects of elastic strain present in the material on the calculated dislocation densities mustbe determined Alternative sources of input data such as the analysis of CBED patterns could provide the elastic strain tensor, allowing for the use of the more complete Nye tensor as defined by Kroner in order to mitigate this problem altogether.

As such, the methods disclosed herein have advantages over both GPA and high resolution EBSD. Since these methods were developed using TEM-based analysis, they are not limited to a particular class of materials or sample geometry. As long as the sample is electron transparent, a diffraction pattern can be generated and thus, precession diffraction can be used. The methods described herein provide a repeatable means of measuring local strain. The technique to calculate a grain boundary driving force and provide a baseline for various strain-driven microstructural evolution processes.

It is to be understood, however, that even though numerous characteristics and advantages of the present invention have been set forth in the foregoing description, together with details of the method, composition and function of the invention, the disclosure is illustrative only, and changes may be made in detail, within the principles of the invention to the full extent indicated by the broad general meaning of the terms in which the appended claims are expressed.

What is claimed is:

1. A method for strain mapping a material comprising the steps of:
   scanning a sample of a material with a transmission electron microscope (TEM), wherein the scanning of the material occurs over multiple steps having a step size and at a beam precession angle;
   comparing each scan at each step and beam precession angle to a template to produce data, wherein the template is generated from parameters of the material and information from the scanning step;

analyzing the data using local mis-orientation mapping analysis or Nye tensor analysis; and producing a local strain map of the sample.

2. The method of 1, wherein the step of analyzing is performed using Nye tensor analysis, and a least squares contortion value is calculated for each of the multiple steps.

3. The method of claim 2, wherein the Nye tensor analysis further comprises estimating a lower bound GND density.

4. The method of claim 2, wherein the Nye tensor analysis further comprises calculating a Nye tensor.

5. The method of claim 1, wherein the step of analyzing is performed using local mis-orientation mapping analysis and further wherein a number n is selected for determining a number of nearest neighbors for each of the multiple steps.

6. The method of claim 5, wherein the number n is selected from the range of 1-10.

7. The method of claim 5, wherein the average mis-orientation between each nearest neighbor for each of the multiple steps is calculated.

8. The method of claim 1, further comprising determining reliability, wherein reliability is a comparison of a best index value with a next best index value.

9. The method of claim 1, wherein the step of analyzing is performed using Nye tensor analysis, wherein each scan at a predetermined step was considered as a center of a kernel with a radius of one and tensor components relating eight nearest neighbors in the kernel were determined.

10. The method of claim 9, wherein a radius of the kernel is from 1-10.

11. The method of claim 1, wherein the predetermined beam precession angle is less than 1.5°.

12. The method of claim 1, wherein the predetermined beam precession angle is from 0.5°-1.0°.

13. The method of claim 1, wherein a step size less than 20 nm by 20 nm.

14. The method of claim 1, wherein the step size is less than 10 nm by 10 nm.

15. The method of claim 1, wherein the material is a polycrystalline material.

16. A method for strain mapping a material comprising the steps of:
scanning a sample of a material with a transmission electron microscope, wherein the scanning of the material occurs over multiple steps having a step size and an angle;

comparing each scan at each step and angle to a template, wherein the template is generated from parameters of the material and information from the scanning, analyzing the data using Nye tensor analysis, wherein a best fit of a Nye tensor for each predetermined step is calculated; and producing a local strain map of the sample.

17. The method of claim 16, wherein the material is a polycrystalline material.

18. The method of claim 17, wherein the step size is less than 10 nm by 10 nm.

19. The method of claim 17, wherein the predetermined beam precession angle is less than 1.5°.

20. The method of claim 16, wherein the Nye tensor analysis further comprises a step of estimating a lower bound GND density.

* * * * *